United States Patent [19]
Griffith

[11] Patent Number: 5,861,035
[45] Date of Patent: Jan. 19, 1999

[54] MODULAR PROSTHETIC CONDUIT

[76] Inventor: Donald P. Griffith, 5696 Longmont Dr., Houston, Tex. 77056

[21] Appl. No.: 862,200

[22] Filed: May 23, 1997

[51] Int. Cl.$^6$ ........................................................ A61F 2/04
[52] U.S. Cl. .................................... 623/12; 623/1; 623/2; 606/191; 606/198; 600/30
[58] Field of Search ..................... 623/1, 2, 12; 606/191, 606/195, 198; 600/29, 30, 31

[56] References Cited

U.S. PATENT DOCUMENTS

| | | | |
|---|---|---|---|
| 4,118,806 | 10/1978 | Porier et al. | 623/2 |
| 4,321,711 | 3/1982 | Mano | 623/1 |
| 5,064,435 | 11/1991 | Porter | 623/12 |
| 5,078,736 | 1/1992 | Behl | 606/198 |
| 5,122,154 | 6/1992 | Rhodes | 623/1 |
| 5,123,917 | 6/1992 | Lee | 623/1 |
| 5,411,551 | 5/1995 | Winston et al. | 623/1 |
| 5,693,087 | 12/1997 | Parodi | 623/12 |
| 5,709,713 | 1/1998 | Evans et al. | 623/1 |

*Primary Examiner*—Paul B. Prebilic
*Attorney, Agent, or Firm*—Rosenblatt & Redano P.C.

[57] ABSTRACT

The present invention relates to a modular prosthetic conduit implantable within a mammal and a method of surgically implanting and replacing such a conduit. Specifically, the present invention is directed toward a conduit comprising a first conduit member composed of a biocompatible alloplast and coated on its exterior surface with a porous biocompatible tissue-bonding material. The present invention is further directed toward a second conduit member composed of a biocompatible alloplast. The second conduit member contains a region or component that can be expanded radially by mechanical, hydraulic, chemical, electrical, temperature sensitive or other physical means. The second component can be easily slid into or out of the first conduit member and at temperatures approaching a mammal's body temperature, it expands to form a watertight "docking" fit within the first conduit member. The second conduit member may contain remotely actuable valve and pump.

Both the first conduit member and the second conduit member may be altered with respect to size, geometry and shape so as to affect conduits, reservoirs, sampling chambers and tissue-prosthesis interfaces. By way of altered size, geometry and shape, the modular prosthetic conduit may serve to drain bodily fluids, give access to intracorporeal organs, deliver drugs or chemicals or energies into the body. Both conduits may be impregnated with antimicrobials to lessen the risk of bacterial colonization.

23 Claims, 3 Drawing Sheets

MODULAR PROSTHETIC CONDUIT

BACKGROUND OF THE INVENTION

1. Field of the Invention

The present invention relates to a modular prosthetic conduit implantable within a mammal and a method of surgically implanting and replacing such a conduit. Specifically, the present invention is directed toward a conduit comprising a first conduit member composed of a nonporous biocompatible alloplast—such as silicone rubber and coated on its exterior surface with a porous biocompatible tissue-bonding material. The present invention is further directed toward a second conduit member composed of a nonporous biocompatible alloplast, such as silicone rubber. The second conduit member contains a region or component that can be expanded radially by mechanical, hydraulic, chemical, electrical, temperaturesensitive or other physical means. This component of the second conduit member may be temperature-sensitive region or component such that at low temperatures, it can be easily slid into or out of the first conduit member, and at temperatures approaching a mammal's body temperature, the temperature sensitive region expands to form a watertight "docking" fit within the first conduit member. The second conduit member may also contain remotely actuable valve and pump.

2. Description of the Prior Art

Implantable prosthetic conduits are frequently used in the field of medicine to provide pathways for transporting fluids or energy. Such conduits may also have other applications, such as the inclusion of reservoirs in the medical sciences. A common problem encountered with medical implants is infection. Proper bonding between the implant and the tissue in which it is implanted is an important factor in avoiding infection.

It is known that biocompatible alloplastic devices coated with porous biocompatible tissue-bonding material, such as porous polytetrafluoroethylene (PTFE), or porous polyurethane, or porous Dacron® (polyethylene terephthalate fiber) or other porous biocompatible alloplasts, effectively bond with epithelial-lined muscular visceral tissues in watertight anastomotic union. Long-term durability of such anastomoses has been achieved in both humans and in animals. Extraluminal porous biocompatible tissue-bonding material, such as polytetrafluoroethylene or porous Dacron® or porous polyurethane or other porous biocompatible alloplasts, in such unions does not usually become colonized with intraluminal bacteria.

Bacterial colonization of porous biocompatible tissue-bonding material is common with porous devices that pass transcutaneously or into body viscera, such as the urinary collecting system. Such colonization leads to the erosion of the anastomoses and loss of any implanted conduit or related prosthetic device.

Nonporous biocompatible alloplast tubes that pass through viscera, such as the epithelial-lined muscular organs, including but not limited to the ureter, bladder, and urethra, and which are anchored extraluminally by porous biocompatible tissue-bonding material, do not usually transmit intraluminal bacteria to the extraluminal porous biocompatible tissue-bonding material. Nonporous biocompatible alloplast tubes, such as silicone tubes, in chronic contact with urine are subject to coating with urinary mucus, encrustation, and stone formation from the dissolved salts contained in the urine. Periodic low morbidity, low-cost replacement of such tubes is desirable.

The present invention is directed toward making implantable medical devices that make effective use of the tissue-bonding properties of porous biocompatible tissue-bonding material, such as polytetrafluoroethylene, polyurethane or polyester fiber, and that also contain a renewable or replaceable nonporous biocompatible alloplast component which can be periodically replaced. A suitable polyester fiber is sold under the trademark Dacron®.

The present invention is directed toward a modular implantable conduit that will allow replacement of the component most likely to become problematic. This invention will decrease the time, expense, and complexity of surgery required to replace such implants.

The present invention also encompasses a surgical method of implanting the conduit. The present invention envisions that the conduit may be used to transport energy (such as electrical, magnetic, or pneumatic), or fluid (such as urine, blood, glandular fluid, or spinal fluid), into or out of the body. The conduit may also be used to transport energy or fluid within or between viscera and other organs. The conduit may contain one or multiple additional components such as reservoirs or sampling chambers. It is also envisioned that the conduit may be used for sampling, evacuating, or adding to body fluids and/or tissues. The present invention may also be a component in a modular system wherein the conduit is attached to a tissue bonding cystostomy tube.

SUMMARY OF THE INVENTION

The present invention is directed toward a modular prosthetic conduit implantable within a mammal, comprising a first conduit member composed of a biocompatible nonporous alloplast and having a distal end and a proximal end. The first conduit member is coated on its exterior surface with a porous, biocompatible tissue-bonding material, such as polytetrafluoroethylene, Dacron®, polyurethane. or any other porous, biocompatible alloplastic material. The first conduit member is intended for permanent implantation in the patient. An advantage of the present invention is that the first conduit member bonds with tissue of the mammal within which it is implanted via fibroblastic ingrowth into the pores of the porous external alloplast, such as porous polytetrafluoroethylene.

The present invention is further directed toward a second conduit member composed of a nonporous biocompatible alloplast such as silicone and having a proximal end, a distal end, and a fixation region located near one or both ends. The second conduit member comprises an expansile-contractile means or component in the fixation region. The expansile-contractile component may be actuated by mechanical, hydraulic, electrical, temperature-sensitive, chemical or other forces.

For example, a thermal expansion material is a shape memory metal such as nitinol, an alloy comprising titanium and nickel. The shape memory material has a first configuration above its transition temperature and a second configuration below its transition temperature. Body heat from the patient can be transferred to the thermal expansion material to cause the temperature of the thermal expansion material to rise above the transition temperature and expand radially. The fixation region thereby docks the second conduit within the first conduit in a watertight fashion. The expansile-contractile component is referred to herein as the "docking component".

The fixation region of the second conduit member has an outer diameter such that during insertion, it is slidably received within the proximal or distal end of the first conduit member, and at actuation, it expands radially outward and makes a watertight fit when inserted into the first conduit member. During insertion and removal, the fixation region is in a contracted mode. During fixation in the first conduit member, the fixation region is in an expanded mode. The expansion and/or contraction of the fixation region is produced by the expansile-contractile component or means. The radial expansion may be actuated by mechanical, hydraulic, electrical, temperature sensitive, chemical, or other forces. The second conduit member is suitable for periodic replacement in the patient.

It is envisioned that in urological applications, the second conduit member will be subjected to daily contact with urine and is expected to become colonized with bacteria, fouled with mucous, and encrusted with urinary salts, such as calcium phosphate. An advantage of the present invention is that the second conduit member can be regularly replaced using the surgical process of the present invention.

The present invention also provides for the inclusion of an extracorporeally or remotely actuated valve and pump assembly within the second conduit member. The valve and pump assembly allow the patient or mammal within which the invention is implanted to volitionally evacuate urine from an interior reservoir. The valve and pump assembly provide a means for volitional evacuation of the bladder. The valve and pump assembly may also be exchanged when the second conduit member is exchanged.

The present invention also provides for the impregnation of both the first conduit member and the second conduit member with antimicrobial drugs, and antiseptics to minimize the risk of bacterial colonization.

The geometry and size of the conduit of the present invention may change as a function of its application. The present invention may serve as a prosthetic urethra, positioned either suprapubically, transpubically, or infrapubically. In this application, silicone disks coated on their exterior surface with a porous biocompatible tissue-bonding material, such as polytetrafluoroethylene, Dacron®, or polyurethane, are placed parallel to and embedded within the detrusor bladder muscle at the proximal end of the first conduit member and within the cavernosal tissue at the distal end of the first conduit member.

The present invention may be used in a variety of modular applications, including but not limited to a urethra alone, a prosthetic ureter alone, an augmented bladder, a total bladder replacement, a prosthetic conduit through the abdominal wall, or a combination of two or more of the above components.

In bladder augmentation or bladder replacement applications, subcutaneous or subsfascial reservoirs are placed in the subcutaneous fat adjacent the inguinal ligament or internal to the abdominal wall muscles. In bladder augmentation applications, the urethral component is not used. Where volitional continence through the prosthetic urethra is desired, the urethral component with a valve and pump assembly will be used.

Both the first conduit member and the second conduit member may be impregnated with antimicrobial drugs and/or antiseptics to minimize the risks of bacterial colonization.

The present invention is also directed toward a method of surgically implanting the modular conduit and of replacing the second conduit member of the modular conduit, as well as any pump or valve assembly installed within the second conduit member.

DETAILED DESCRIPTION OF THE PREFERRED EMBODIMENTS

The apparatus embodiment of the present invention is directed toward a modular prosthetic conduit implantable within a mammal, comprising a first conduit member 30 composed of a nonporous biocompatible alloplast such as silicone and having a distal end 30a and a proximal end 30b. The first conduit member is coated on its exterior surface with a porous biocompatible tissue-bonding material 59. In a preferred embodiment, this material is porous polytetrafluoroethylene or porous polyurethane or Dacron ® or other porous biocompatible alloplasts.

Figure 1A:
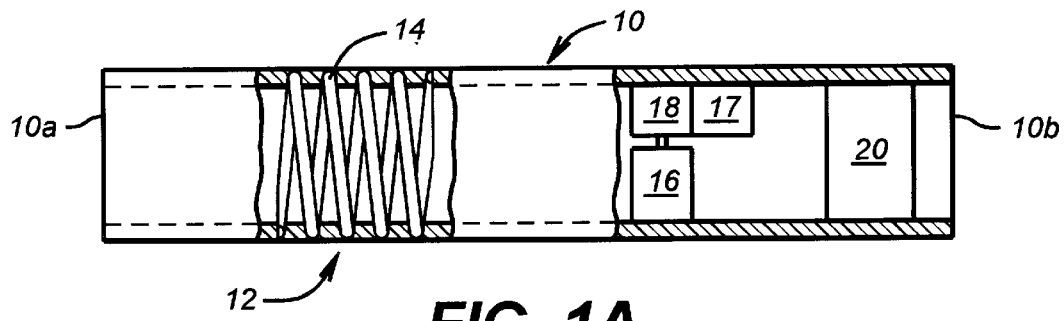
FIG. 1A is a side cutaway view of a first embodiment of the second conduit member of the present invention.
Figure 1B:
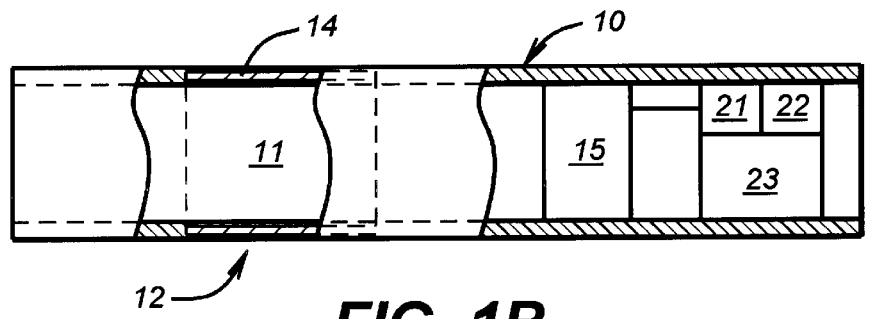
FIG. 1B is a side cutaway view of a second embodiment of the second conduit member of the present invention.

The invention further comprises a second conduit member 10 composed of a nonporous biocompatible alloplast such as silicone and having a proximal end 10a, a distal end 10b, and a fixation region 11 located near one or both ends. The second conduit member comprises an expansile-contractile means or component within the wall of the fixation region. The fixation region of the second conduit member has an outer diameter such that during insertion it is slidably received within the first conduit member, and after actuation, it makes a watertight fit when inserted into the second conduit member. As shown in FIGS. 1A and 1B, the second conduit member is open at both ends.

Figure 2A:
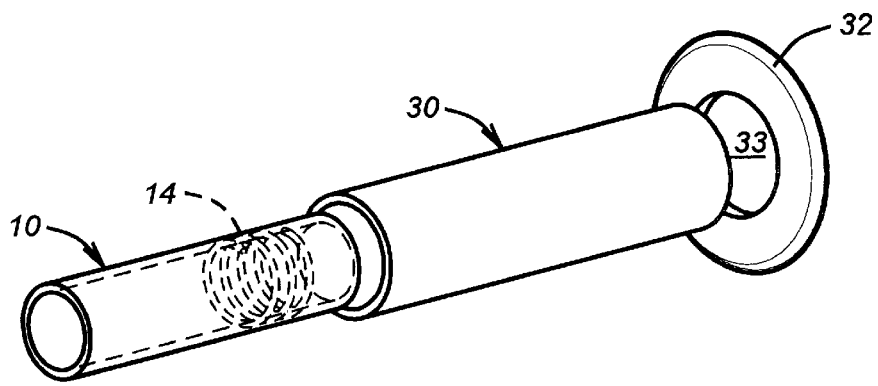
FIG. 2A is an exploded isometric view of the present invention.
Figure 2B:
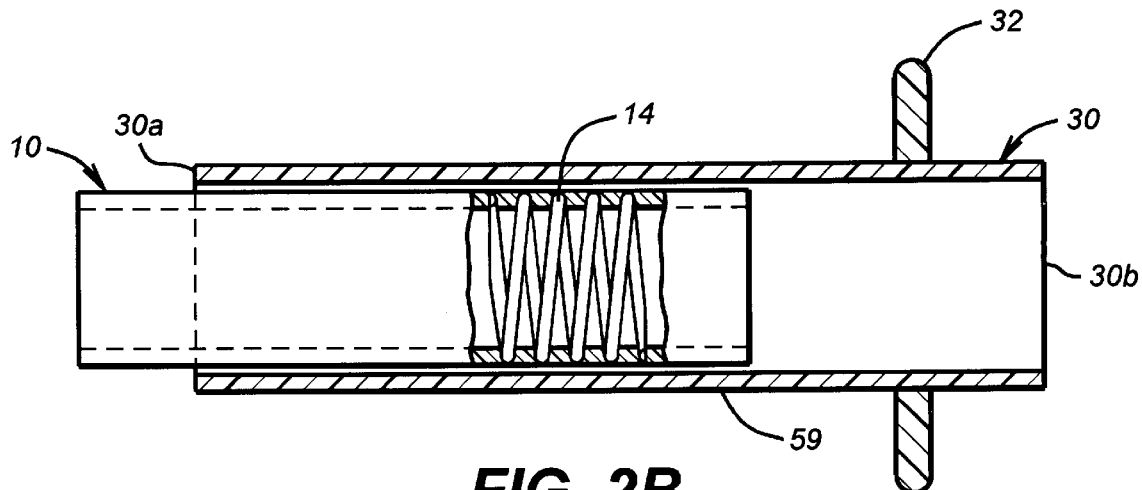
FIG. 2B is a side cutaway view of an embodiment of the present invention.

In a preferred embodiment, the expansile-contractile means or component is a temperature sensitive component wherein radial expansion and fixation occur within the range of 35° C. to 38° C. In a preferred embodiment, temperature sensitive component is a helical wire, cylinder, strip, or tube of metal 14, as shown in FIGS. 1A and 1B. The thermal expansion material may also comprise nitinol. As shown in FIG. 2A, the expansile-contractile means or component 14 may be integrally formed in the fixation region of the second conduit member.

When the temperature of the thermal expansion material is reduced from a temperature above the transition temperature to a temperature below the transition temperature, the fixation region of the second conduit member shrinks such that it is slidably removable from the first conduit member. When the temperature of the thermal expansion material is raised from a temperature below the transition temperature to a temperature above the transition temperature, the fixation region of the second conduit member expands such that it forms a watertight fit when the second conduit member is inserted into the first conduit member. These expansion and contraction characteristics of the second conduit member allow it to be easily replaced after implantation into a patient.

In a preferred embodiment the expansile-contractile means may be mechanical, hydraulic, electrical or chemical wherein the expansile-contractile region expands to dock the second conduit member in a watertight fashion into the first conduit member.

In a preferred embodiment, the invention further comprises a remotely actuable valve assembly 15 slidably inserted within the second conduit member. The valve assembly may be mechanical or electromechanical and can be actuated extracorporeally. In a preferred embodiment, the remotely actuable valve assembly comprises an electromechanical valve 16, a valve controller 18 configured to open or close the valve in response to a control signal, and a signal receiver 17 capable of receiving a remotely generated control signal, processing that signal, and sending that signal to the valve controller, as shown in FIGS. 1A and 1B.

In another preferred embodiment, the valve may be mechanical. In this embodiment, the valve may be opened or closed using extracorporeally or intracorporeally applied pressure. A finger inserted vaginally is one method of applying pressure intracorporeally to an intraurethral valve.

In another preferred embodiment, the invention further comprises a remotely actuable pump assembly 20 slidably inserted in the second conduit member. The pump assembly can be actuated extracorporeally. In a preferred embodiment, the pump assembly comprises a pump 23, a pump controller 22 configured to turn the pump on or off, and a signal receiver 21 capable of receiving a remotely generated control signal, processing that signal and sending that signal to the pump controller, as shown in FIGS. 1A and 1B.

In another embodiment, the invention may comprise both a remotely actuable valve and pump inserted in the second conduit member, and a controller coupled to the valve and the pump, as shown in FIGS. 1A and 1b. In a preferred embodiment, the pump and valve assembly sold under the mark U/FLOWM™ by Influence, Inc., may be used.

In a preferred embodiment, the invention further comprises a disk or patch 32 composed of a biocompatible alloplast, coated on its exterior surface with a porous biocompatible alloplast, such as polytetrafluoroethylene, or polyurethane or other porous biocompatible alloplast comprising a central opening 33 through which the first conduit member is slidably insertable. This opening is sized to snugly receive the first conduit member.

Figure 3A:
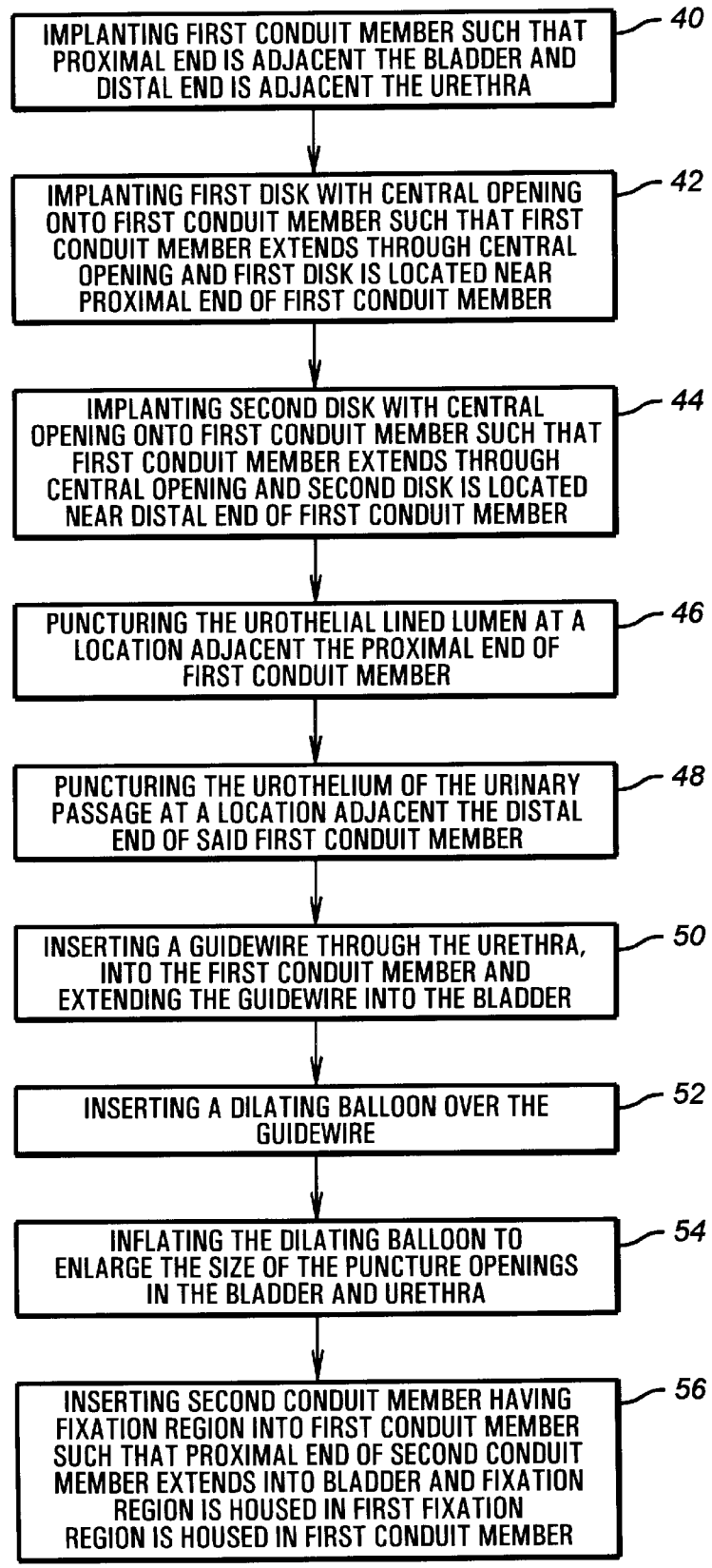
FIG. 3A is a block diagram of a first embodiment of the surgical implantation procedure of the present invention.

The present invention also extends to a method for implanting the modular conduit. As shown in FIG. 3A, the first step in the process 40 is surgically implanting a first conduit member having a proximal end and a distal end and composed of a nonporous biocompatible alloplast, such as silicone rubber and coated on its exterior surface with a porous biocompatible tissue-bonding material, such that the proximal end of the first conduit member is adjacent the bladder and the distal end of the first conduit member is adjacent the urethra.

The second step 42 of the surgical process is surgically implanting a first disk or patch composed of silicone and coated on its exterior surface with a porous, biocompatible, tissue-bonding material and further containing a central opening onto the first conduit member such that the first conduit member extends through the central opening and the first disk or patch is located near the proximal end of the first conduit member.

The third step 44 of the surgical process is surgically implanting a second disk or patch composed of silicone and coated on its exterior surface with a porous, biocompatible, tissue-bonding material and further containing a central opening onto the first conduit member such that the first conduit member extends through the central opening and the second disk or patch is located near the distal end of the first conduit member.

In a preferred embodiment, the first three steps 40, 42 and 44 may be performed by means of percutaneous endoscopic techniques. Such endoscopic techniques may employ fluoroscopy, contrast media, trocars, dilating balloons and catheters all of which are well known to the skilled and experienced endoscopic surgeon.

In a preferred embodiment, a time period of two to six months usually elapses between the completion of the third step and the start of the fourth step. This time period permits fibroblasts from the fascia and muscular tissue in contact with the first conduit member to grow into the pores of the first conduit member, resulting in an effective tissue bond with the first conduit member. The actual length of this time period varies from patient to patient, according to the surgeon's judgment. Factors such as an absence of redness, swelling, and tenderness in the vicinity of the first conduit member and no fluctuance over the first conduit member indicate that satisfactory fibroblastic bonding has occurred with the first conduit member and the fourth step may be performed.

If during this time delay, redness, swelling, or tenderness are detected in the vicinity of the first conduit member, the surgeon may elect to discontinue this procedure and remove the first conduit member.

The fourth step 46 of the surgical process is surgically puncturing the urothelial-lined lumen at a location adjacent the proximal end of the first conduit member. The fifth step 48 of the surgical process is surgically puncturing the urothelium of the urinary passage at a location adjacent the distal end of the first conduit member. Both the fourth step 46 and the fifth step 50 may be performed surgically, endoscopically, or fluoroscopically. In a preferred embodiment it is accomplished endoscopically or fluoroscopically.

The sixth step 50 of the surgical process is inserting a guidewire into the urethral meatus, then into the urethra, and then through the first conduit member and extending the guidewire into the bladder. The seventh step 52 of the surgical process is inserting a dilating balloon over the guidewire. The eighth step 54 of the surgical process is inflating the dilating balloon such that it expands and enlarges the size of the puncture openings made in the urothelium of the bladder and uretha.

The ninth step 56 of the surgical process is inserting a second conduit member composed of a nonporous biocompatible alloplast and having a proximal end, a distal end, and a fixation region located near one or both of its ends into the first conduit member such that the proximal end of the second conduit member extends into the bladder and the fixation region is housed within the first conduit member.

Figure 3B:
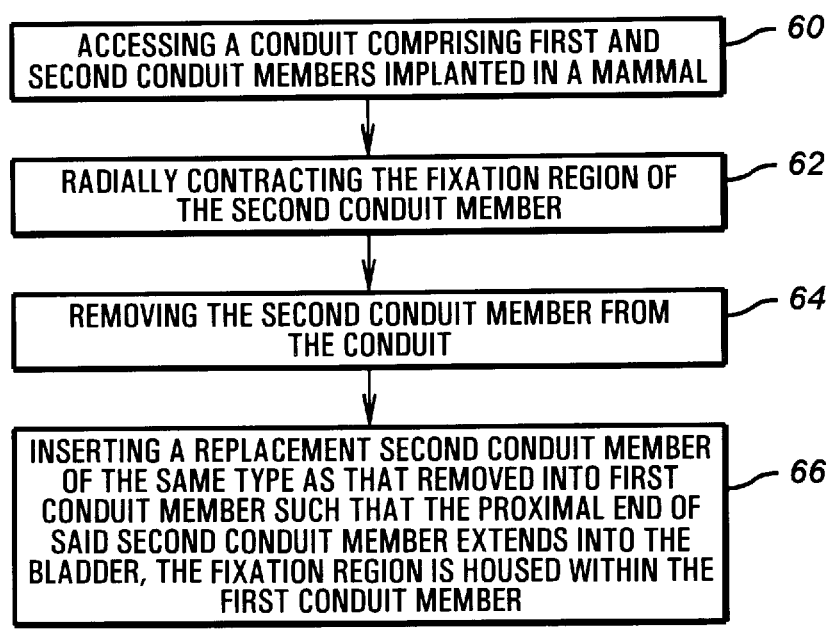
FIG. 3B is a block diagram of a second embodiment of the surgical implantation procedure of the present invention.

A second embodiment of the surgical process of the present invention is shown in FIG. 3B. This embodiment is directed toward replacing the second conduit member of a modular conduit implanted in a mammal. This embodiment of the present invention is applicable after a second conduit member has already been implanted within a first conduit member in a mammal, as described above.

In the first step of this process 60 a conduit comprising first and second conduit members implanted within a mammal is accessed. This accessing is performed surgically, fluoroscopically or endoscopically.

The second step of this process 62 comprises radially contracting the fixation region or component via hydraulic, mechanical, electrical, chemical or temperaturesensitive means. This step of the process of the present invention results in a contraction, shrinkage, or relaxation of the fixation region of the second conduit member, thereby allowing it to be easily removed from the first conduit member.

The third step 64 of this process comprises removal of the second conduit member from the first conduit member. In a preferred embodiment, this removal can be accomplished endoscopically or fluoroscopically.

The fourth step 66 of this process comprises inserting a replacement second conduit member of the type just removed into the first conduit member such that the distal end of the second conduit member extends into the bladder and the fixation region is housed within the first conduit member. In this step, the replacement second conduit member is implanted within the mammal.

The fifth step 68 of the present invention comprises radially expanding the fixation region or component. This step results in an expansion of the expansilecontractile region, such that the replacement second conduit member forms a watertight fit with the first conduit member at the fixation region.

The foregoing disclosure and description of the invention are illustrative and explanatory thereof, and various changes in the size, shape and materials, as well as in the details of the illustrated construction, may be made without departing from the spirit of the invention.

I claim:

1. A modular prosthetic conduit implantable within a mammal, comprising:
   a. a first conduit member composed of a biocompatible nonporous alloplast and coated on its exterior surface with a porous, biocompatible tissue-bonding material; and
   b. a second conduit member having two open ends and composed of a biocompatible nonporous alloplast and having a fixation region comprising an expansilecontractile component, said fixation region having an outer diameter such that it is slidably received within said first conduit member when said fixation region is in a contracted mode and said fixation member is capable of making a watertight fit in said first conduit member, when said fixation region is in an expanded mode.

2. The conduit of claim 1 wherein said expansile-contractile component comprises a thermal expansion material comprising a shape memory material having a transition temperature such that at temperatures below the transition temperature, the fixation region is in a contracted mode and at temperatures above the transition temperature, the fixation region is in an expanded mode.

3. The conduit of claim 2, wherein said thermal expansion material is a helical strip of metal or a metallic tube.

4. The conduit of claim 2, wherein when the temperature of said thermal expansion material is reduced from a temperature above the transition temperature to a temperature below the transition temperature, the fixation region of said second conduit member shrinks such that it is slidably removable from said first conduit member.

5. The conduit of claim 2, wherein said thermal expansion material comprises nitinol.

6. The conduit of claim 1, wherein said porous biocompatible tissue bonding material is any biocompatible, porous tissue bonding alloplast and said expansile-contractile component is integrally formed in said fixation region.

7. The conduit of claim 1, further comprising a remotely actuatable valve assembly slidably inserted within said second conduit member.

8. The conduit of claim 1 wherein said first conduit member and said second conduit members are impregnated with antimicrobial drugs or antiseptics.

9. The conduit of claim 7, wherein said valve assembly comprises:
   a. a valve;
   b. a valve controller configured to open or close said valve in response to a control signal; and
   c. a signal receiver capable of receiving a remotely generated control signal, processing said signal and sending said signal to said valve controller.

10. The conduit of claim 7, wherein said valve assembly comprises:
    a. a valve; and
    b. a valve controller configured to open or close said valve in response to a predetermined amount of pressure.

11. The conduit of claim 10, wherein said pressure is extracorporeal.

12. The conduit of claim 10, wherein said pressure is intracorporeal.

13. The conduit of claim 7, wherein said conduit further comprises a remotely actuatable pump assembly slidably inserted in said second conduit member.

14. The conduit of claim 7, wherein said pump assembly comprises:
    a. a pump;
    b. a pump controller configured to turn said pump on or off; and
    c. a signal receiver capable of receiving a remotely generated control signal, processing said signal, and sending said signal to said pump controller.

15. The conduit of claim 1, further comprising:
    a. a remotely actuatable valve inserted in said second conduit member;
    b. a remotely actuatable pump inserted in said second conduit member; and
    c. a controller coupled to said valve and to said pump.

16. The conduit of claim 15, further comprising a disk coated on its exterior surface with a porous, biocompatible alloplast and comprising a central opening through which said first conduit member is slidably inserted, said opening is sized to snugly receive said first conduit member.

17. The conduit of claim 1 wherein said expansile-contractile component is capable of being radially expanded by mechanical, hydraulic, electrical, or chemical means.

18. A modular prosthetic conduit implantable within a mammal, comprising:
    a. a first conduit member composed of a biocompatible alloplast and coated on its exterior surface with a porous, biocompatible tissue-bonding material;
    b. a second conduit member having two open ends and composed of a nonporous biocompatible alloplast, and having a fixation region, said fixation region having an outer diameter such when said fixation region is in a contracted mode, it is slidably received within the first conduit member and when said fixation region is in an expanded mode, it makes a watertight fit when inserted in said first conduit member; and
    c. an expansile-contractile component within said fixation region.

19. The conduit of claim 18, wherein said expansile-contractile component is a shape memory metal having a helical or cylindrical shape.

20. The conduit of claim 18, further comprising a remotely accuatable pump assembly slidably inserted in said second conduit member.

21. The conduit of claim 18, wherein said porous biocompatible tissue bonding material is any biocompatible porous tissue bonding alloplast.

22. The conduit of claim 18, further comprising a remotely a remotely accuatable pump assembly slidably inserted in said second conduit member.

23. The conduit of claim 18, wherein said expansile-contractile component is integrally formed in said fixation region.

* * * * *